United States Patent [19]

Fuess

[11] Patent Number: Plant 7,724

[45] Date of Patent: Nov. 26, 1991

[54] CHRYSANTHEMUM PLANT NAMED GOLD RUSH

[76] Inventor: Janet S. Fuess, 9011 Red Hill Rd., New Hartford, N.Y. 13413

[21] Appl. No.: 543,381

[22] Filed: Jun. 26, 1990

[51] Int. Cl.[5] ..... A01H 5/00

[52] U.S. Cl. ..... Plt./74

[58] Field of Search ..... Plt./74, 82.2, 82.3, Plt./82.4, 76, 79

*Primary Examiner*—Howard J. Locker

*Attorney, Agent, or Firm*—Foley & Lardner

[57] ABSTRACT

A Chrysanthemum plant named Gold Rush particularly characterized by its bicolored honey-bronze daisy flowers, compact cushion habit, free branching and flowering, outstanding keeping quality, seven week response in photoperiodic programs, and its suitability for use as a garden chrysanthemum.

1 Drawing Sheet

The present invention comprises a new and distinct cultivar of Chrysanthemum, botanically known as *Dendranthema grandiflora,* and referred to by the cultivar name Gold Rush.

Gold Rush is a product of a planned breeding program which had the objective of creating new Chrysanthemum cultivars with a freely branching, compact cushion habit, early flower response, bicolored honey-bronze daisy flowers, and having a suitability for production as a greenhouse or garden variety. Such traits in combination were not present in previously available commercial cultivars.

Gold Rush was originated from a hybridization made in a controlled breeding program in New Hartford, N.Y. in September 1987. The female parent was the cultivar Cornhusker (U.S. Plant Pat. No. 6,401). The male parent of Gold Rush was a purple decorative identified as A86-26.

Gold Rush was discovered and selected as one flowering plant without the progeny of the stated parentage by applicant in September 1988 in a controlled environment in New Hartford, N.Y.

The first act of asexual reproduction of Gold Rush was accomplished when vegetative cuttings were taken from the initial selection in September 1988 in a controlled environment in New Hartford, N.Y., by a technician working under formulations established and supervised by applicant.

Horticultural examination of selected units initiated in August 1989 has demonstrated that the unique combination of characteristics as herein disclosed for Gold Rush are firmly fixed and are retained through successive generations of asexual reproduction.

Gold Rush has not been observed under all possible environmental conditions. The phenotype may vary significantly with variations in environment such as temperature, light intensity and daylength. The following observations, measurements and comparisons describe plants grown in Carpinteria, Calif. and under greenhouse conditions which approximate those generally used in commercial greenhouse practice.

The following traits have been repeatedly observed and are determined to be basic characteristics of Gold Rush which, in combination, distinguish this Chrysanthemum as a new and distinct cultivar:

1. Honey-bronze ray floret color, having a distinctive two-tone effect.

2. A multiplex daisy inflorescence.
3. Fully expanded ray florets approximately 2 cm. long and 0.5 cm. wide.
4. Average of 80–85 ray florets per capitulum.
5. Capitulum 4–5 cm. in diameter.
6. Seven week flower response in light/shade (photoperiodic) programs.
7. Compact cushion habit, making it suitable for production in 4" to 8" containers.
8. Freely branching and flowering.
9. Outstanding keeping quality.
10. Adaptability to greenhouse or garden cultures.

Of the many commercial cultivars known to the present inventor, the most similar in comparison to Gold Rush is the female parent Cornhusker. In comparison to Cornhusker, Gold Rush has a more compact cushion habit, a distinctive two-tone effect, a one week earlier response in light/shade programs, and a natural season flowering date twelve days earlier than Cornhusker. The plant spread of Gold Rush is similar to the plant spread of Cornhusker.

The accompanying photographic drawing comprises a relatively closeup view of typical inflorescence and the foliage shape of Gold Rush. The flower color accurately depicts true color and is consistent with the values appearing below. The illustrated foliage color is not accurate, being almost blue in color as opposed to the actual dark green foliage color, the true color values of which are noted below.

In the following description color references are made to The Royal Horticultural Society Colour Chart. The color values were determined between 1:00 and 3:00 p.m. on Mar. 7, 1990 under 4,000 foot candles at Carpinteria, Calif.

Classification:

*Botanical.*—*Dendranthema grandiflora* cv Gold Rush.

*Commercial.*—Garden mum and daisy spray pot mum.

INFLORESCENCE

A. Capitulum:

*Form.*—Daisy.

*Type.*—Multiplex-bicolored.

*Diameter across face.*—4–5 cm.

B. Corolla of ray florets: 80–85 florets.

*Color (general tonality from a distance of three meters).*—Bronze, 167 A-B.

*Color (under surface).*—0.3 cm. center stripe, 21B; long edges, 14C.

*Color (upper surface).*—Immature, 168B; mature 167A-B with bright yellow tip and strip of yellow running 3 mm. along the edge.

*Size.*—2 cm. long and 0.5 cm. wide; irregular tridentate tip.

*Bud.*—172B.

C. Corolla of disc florets: 65–75 florets.

*Color (mature).*—17A.

*Color (immature).*—17B.

*Size.*—0.6 cm. long and 0.15 cm. wide; tubular, 7 pointed.

D. Reproductive organs:

*Androecium.*—Present on disc florets only; 5–7 stamens, 0.35 cm.; filaments separate; anther sacs attached; clasping style.

*Gynoecium.*—Ray: Style, 0.4 cm., bifurcated; gold stigma; white ovule, 1 mm. long. Disc: Style 0.5 cm.; white ovule, 1 mm. long.

PLANT

A. General appearance:

*Height.*—25–35 cm. when grown in an 8″ container.

B. Foliage:

*Color (under surface).*—147B.

*Color (upper surface).*—147A.

*Size.*—3–5 cm. long and 3–4 cm. wide.

*Shape.*—5 lobed-rounded; smooth margin with minute point at end of lobe.

I claim:

1. A new and distinct cultivar of Chrysanthemum plant named Gold Rush, as described and illustrated.

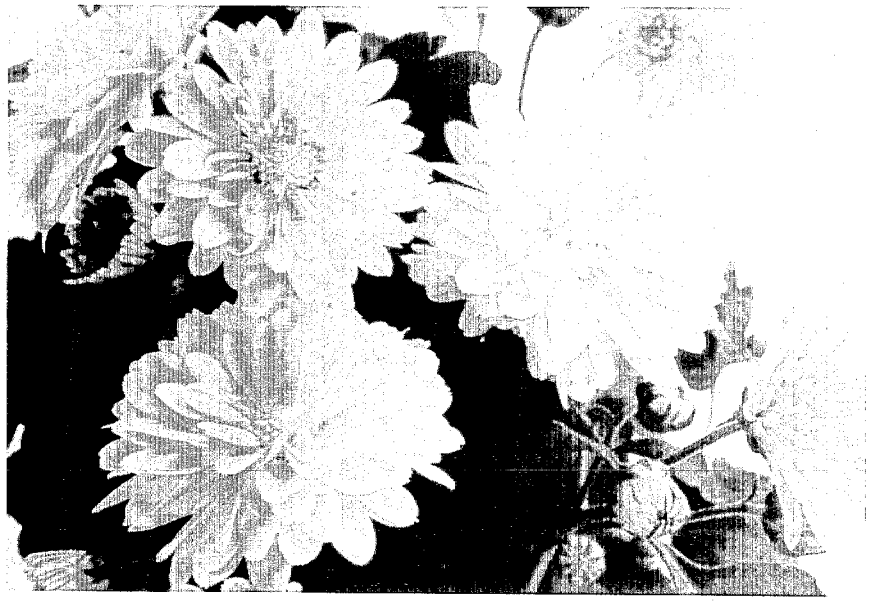

* * * * *